(12) United States Patent
Shibata et al.

(10) Patent No.: US 8,663,559 B2
(45) Date of Patent: Mar. 4, 2014

(54) SAMPLE ANALYZER, SAMPLE ANALYZING METHOD, AND COMPUTER PROGRAM PRODUCT

(75) Inventors: Masaharu Shibata, Kobe (JP); Noriyoshi Yoshida, Kobe (JP)

(73) Assignee: Sysmex Corporation, Kobe (JP)

( * ) Notice: Subject to any disclaimer, the term of this patent is extended or adjusted under 35 U.S.C. 154(b) by 665 days.

(21) Appl. No.: 12/079,825

(22) Filed: Mar. 28, 2008

(65) Prior Publication Data

US 2008/0241957 A1 Oct. 2, 2008

(30) Foreign Application Priority Data

Mar. 29, 2007 (JP) ................. 2007-089642

(51) Int. Cl.
*G01N 15/06* (2006.01)

(52) U.S. Cl.
USPC ............... 422/68.1; 422/50; 422/63; 422/64; 422/65; 422/66; 422/67; 422/81; 422/82.01; 422/82.05; 436/43; 436/47; 436/54; 436/63; 436/66

(58) Field of Classification Search
USPC ........... 422/50, 63, 64, 65, 66, 67, 81, 82.01, 422/82.05, 68.1; 436/43, 47, 54, 63, 66, 67, 436/68, 69, 70, 71, 174, 180
See application file for complete search history.

(56) References Cited

U.S. PATENT DOCUMENTS

| | | | |
|---|---|---|---|
| 2004/0101440 A1* | 5/2004 | Ishizawa et al. | 422/64 |
| 2005/0053521 A1* | 3/2005 | Hirayama | 422/67 |
| 2005/0196821 A1* | 9/2005 | Monfre et al. | 435/14 |
| 2006/0029520 A1* | 2/2006 | Tanoshima et al. | 422/63 |
| 2006/0210438 A1* | 9/2006 | Nagai et al. | 422/73 |
| 2007/0078631 A1* | 4/2007 | Ariyoshi et al. | 702/189 |
| 2007/0110617 A1* | 5/2007 | Nagai et al. | 422/65 |
| 2008/0056944 A1* | 3/2008 | Nakamura et al. | 422/67 |
| 2008/0187951 A1* | 8/2008 | Nagai et al. | 435/29 |
| 2008/0206098 A1* | 8/2008 | Tsutsumida et al. | 422/67 |
| 2009/0035873 A1* | 2/2009 | Shibata | 436/179 |

* cited by examiner

*Primary Examiner* — Brian J Sines
(74) *Attorney, Agent, or Firm* — Brinks Gilson & Lione (57) ABSTRACT

A sample analyzer that includes a sample preparing section operative to aspirate a sample from a sample container and a measuring section operative to prepare a plurality of measurement samples from the aspirated sample. A control unit is configured to sequentially measure the plurality of prepared measurement samples, obtain a plurality of measurement data for the respective measurement samples, and obtain an analysis result of a predetermined item of the sample based on the plurality of measurement data.

10 Claims, 10 Drawing Sheets

SAMPLE ANALYZER, SAMPLE ANALYZING METHOD, AND COMPUTER PROGRAM PRODUCT

RELATED APPLICATIONS

This application claims priority under 35 U.S.C. §119 to Japanese Patent Application No. JP2007-089642 filed Mar. 29, 2007, the entire contents of which are hereby incorporated by reference.

FIELD OF THE INVENTION

The present invention relates to a sample analyzer, sample analyzing method, and computer program product.

BACKGROUND

High-precision analysis is demanded of sample analyzers. For example, Japanese Laid-Open Patent Publication No. 4-84770 discloses an electrolyte measuring apparatus for improving analysis accuracy. This electrolyte measuring apparatus improves analysis accuracy by repeating measurements until the difference in the measurement values of two consecutive measurements are within a set value range.

Automatic multifunction hemocyte analyzers are known (for example, model XE-2100 (Sysmex Corporation)) which automatically performs a PLT double count when the count value of blood platelets (PLT) is below a set value. In the PLT double count, PLT are counted using a double quantity of the sample used in a normal measurement. High precision analysis is therefore possible even when there is a low concentration of the substance being measured in the sample.

In the electrolyte measuring apparatus disclosed in Japanese Laid-Open Patent Publication No. 4-84770, however, high precision analysis results are difficult to obtain due to the wide variation in the measurement values of the individual measurements when there is a low concentration of the substance being measured in the sample.

In the automatic multifunction hemocyte analyzer above, a double quantity of reagent must be added to correspond to the double quantity of sample used in a normal measurement. Therefore a reagent mixing chamber which accommodates double the normal quantity of reagent, and a dosage pump which delivers double the normal quantity of reagent to the reagent mixing chamber are required, and result in increasing the overall size of the apparatus. Furthermore, although the amount of reagent used must be increased in order to perform high precision analysis even when the count value of the PLT in the sample is extremely low (for example, five times the normal quantity of reagent), there are limits to the increase in size of the reagent mixing chamber and dosage pump. It therefore can not be said that that measurement accuracy of this automatic multifunction hemocyte analyzer is adequate in the case of samples which have very low concentrations of a measurement substance.

SUMMARY OF THE INVENTION

The scope of the present invention is defined solely by the appended claims, and is not affected to any degree by the statements within this summary.

A first aspect of the present invention is a sample analyzer comprising: a retaining section for retaining a sample aspirated from a sample container; a sample preparing section for preparing a plurality of measurement samples from the sample retained in the retaining section; a measuring section for sequentially measuring the plurality of measurement samples prepared by the sample preparing section, and obtaining a plurality of measurement data of the respective measurement samples; and an analysis result obtaining means for obtaining an analysis result of a predetermined item of the sample based on the plurality of measurement data obtained by the measuring section.

A second aspect of the present invention is a sample analyzing method comprising: aspirating a sample from a sample container; preparing a plurality of measurement samples from the aspirated sample; sequentially measuring the plurality of prepared measurement samples; obtaining a plurality of measurement data for the respective measurement samples; and obtaining an analysis result of a predetermined item of the sample based on the plurality of measurement data.

A third aspect of the present invention is A computer program product, comprising: a computer readable medium; and instructions, on the computer readable medium, adapted to enable a sample analyzer to perform operations, comprising: obtaining a plurality of measurement data for respective measurement samples, wherein the respective measurement samples are obtained by sequentially measuring a plurality of measurement samples prepared from a sample container; and obtaining an analysis result of a predetermined item of the sample based on the plurality of measurement data.

DETAILED DESCRIPTION OF THE PREFERRED EMBODIMENTS

The preferred embodiments of the present invention will be described hereinafter with reference to the drawings.

Figure 1:
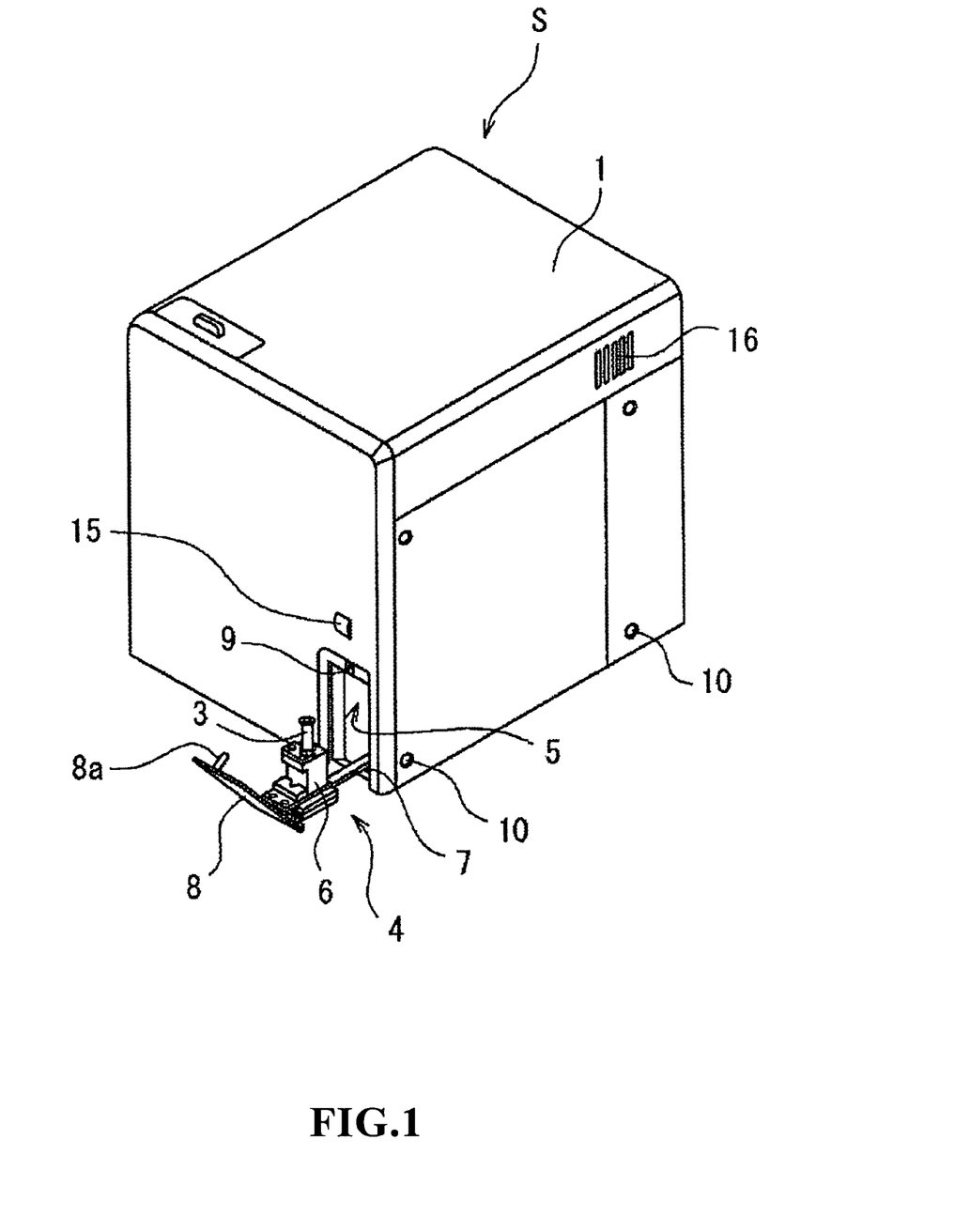
FIG. 1 is a general perspective view of an embodiment of the sample analyzer of the present invention.
Figure 2:
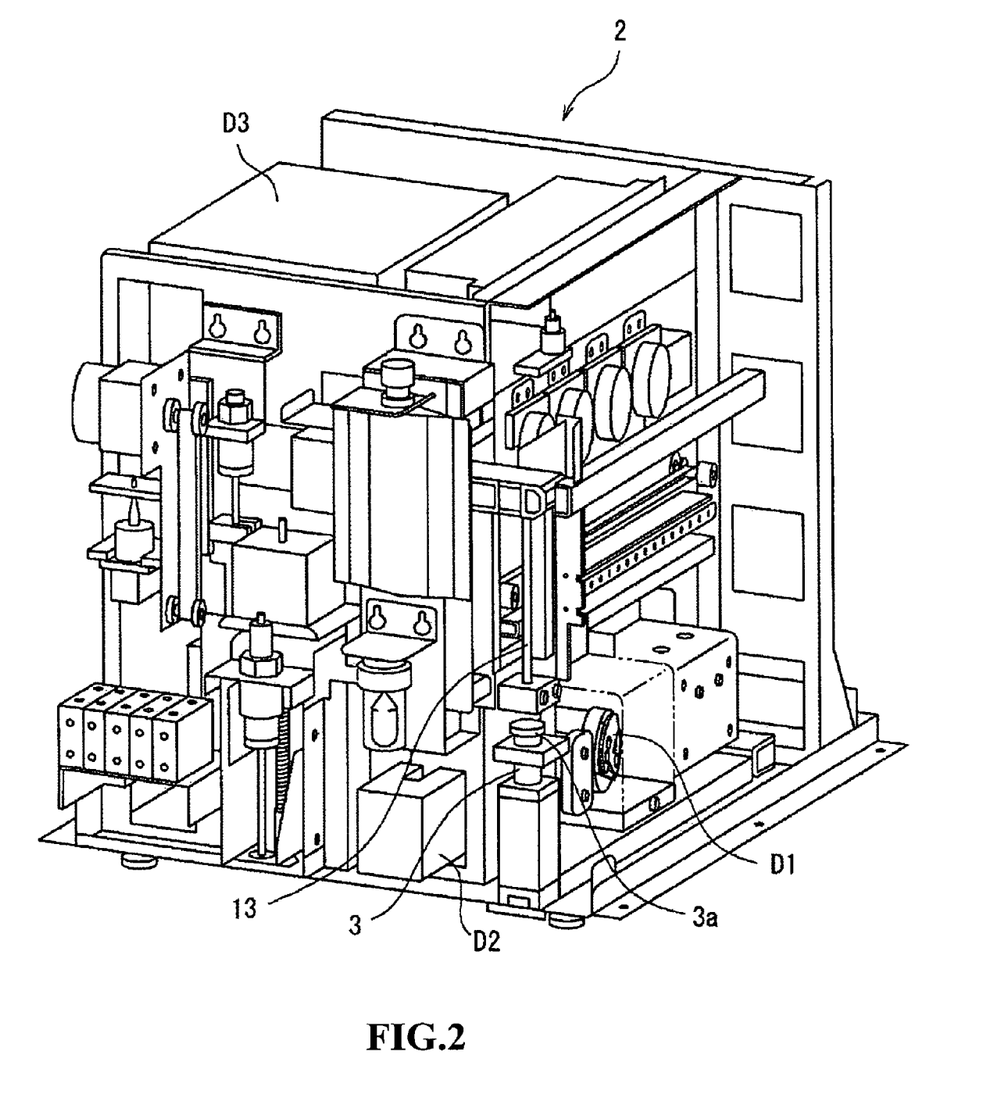
FIG. 2 is a perspective view of the sample analyzer of FIG. 1 with the casing removed.
Figure 3:
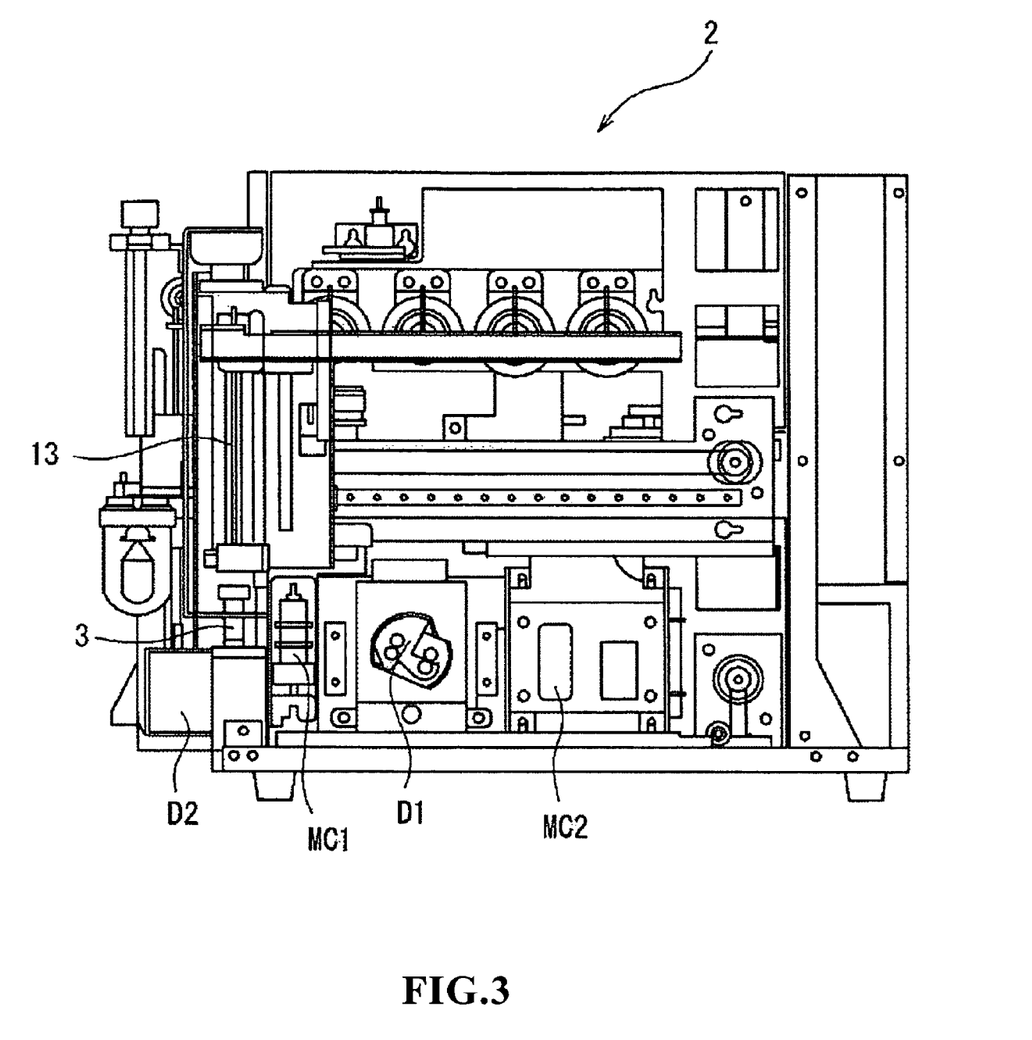
FIG. 3 is a right side view of the sample analyzer of FIG. 1 with the casing removed.

FIG. 1 is a general perspective view of a sample analyzer S of an embodiment of the present invention, FIG. 2 is a perspective view of the sample analyzer S with a casing 1 removed, and FIG. 3 similarly is a view from the right side with the casing removed.

The sample analyzer S is an apparatus for analyzing blood cell components (red blood cells (RBC), white blood cells (WBC), platelets (PLT), and hemoglobin (Hgb)) contained in a sample. The samples analyzed by the sample analyzer S are not particularly limited inasmuch as blood, urine, body fluids (abdominal fluid, cerebral fluid, thoracic fluid and the like), and platelet products and the like may also be analyzed.

The sample analyzer S is connected to a processing device PC (typically, a personal computer on which is installed a required computer program) which has a display, input device, and CPU, memory and the like so as to be capable of communication, and a sample analyzing system is formed by the sample analyzer S and the processing device PC.

The processing device PC contains installed sample analyzer software for operating the sample analyzer S, various settings related to analyses, displaying analysis results and the like, and is capable of sending instructions to the sample analyzer S, and receiving measurement data from the sample analyzer S via communication between the sample analyzer S and the processing device PC.

The sample analyzer S is a sample analyzer which analyzes samples contained in sample containers 3, and is mainly configured by an apparatus body 2, and a casing 1 which houses the apparatus body 2.

The casing 1 is manufactured of synthetic resin, rust-proof steel plate and the like, and is attached to the apparatus body 2 by fixing means such as bolts. An opening 5 is formed at the lower right side on one side of the casing 1 (left side surface in FIG. 1), so that the sample containers 3 can be inserted into the apparatus body 2 through this opening 5. That is, a slider 7 is disposed at one end at the bottom of the apparatus body 2 so as to be capable of freely extending and retracting from the opening 5, and on which is disposed a mounting base 6 for holding a sample container 3 near the end part thereof. A cover 8, which closes the opening 5, is provided so as to be freely rotatable at the leading end of the slider 7, and a spring which is not shown in the drawing exerts a force to incline the cover 8 outwardly at a predetermined angle (refer to FIG. 1). When a button 15 is pressed when the apparatus is not operating (this condition is indicated on the outside of the apparatus by an unlighted lamp within the button 15 provided on one side of the casing 1), the slider 7 is extended outward from the apparatus body 2. Although the opening 5 is closed by the cover 8 when the apparatus is not operating, the engagement a projection 8a of the cover 8 and a concavity 9 formed on the periphery of the opening 5 is released by advancing the slider 7 to the outside of the apparatus body 2, and the cover 8 thus opens. The cover 8 is then outwardly inclined at a predetermined angle by the force exerted by the spring when the engagement of the projection 8a and the concavity 9 is released.

A concavity (not shown in the drawing) is formed on the top surface of the mounting base 6 to accept the insertion of the bottom part of the sample container 3, when a sample container 3 is inserted in this concavity and the button 15 is pressed, the slider 7 is retracted into the apparatus body 2 and sets the sample container 3 at a predetermined position. Then, the cover 8 stands up against the force exerted by the spring and the opening 5 is closed by the cover 8. The cover 8 is prevented from opening by the engagement of the previously mentioned projection 8a and the concavity 9. Since the certain closing of the opening 5 by the cover 9 is detected by a detecting means such as a microswitch or the like, a subsequent sample aspirating process is enabled.

A part of the side surface of the casing 1 (the surface on the right side in FIG. 1 is fixedly attached to the apparatus body 2 by bolts 10 for ease of maintenance and inspection within the apparatus body 2. In FIG. 1, reference number 16 refers to an exhaust port through which the heat generated within the apparatus body 2 is expelled to the outside by a fan (not shown in the drawing).

The sample analyzer S is provided with a sample receiving part 4 at which the sample container 3 is placed at a predetermined position within the apparatus, and measuring sections D1, D2, and D3 for measuring a measurement sample prepared from a sample aspirated from the sample container 3 placed at the sample receiving part 4.

The sample analyzer S is further provided with an aspirating tube (pipette) 13, a first mixing chamber MC1, and second mixing chamber MC2. A sample, which has been aspirated by the aspirating tube 13 from a sample container 3 set at the sample receiving part 4, is respectively dispensed to the first mixing chamber MC1 and second mixing chamber MC2. Measurement samples are respectively prepared using reagents in the first mixing chamber MC1 and second mixing chamber MC2. The measurement sample prepared by the first mixing chamber MC1 is used for measurements by the measuring sections D1 and D2, and the measurement sample prepared by the second mixing chamber MC2 is used for measurement by the measuring section D3.

The measuring section D1 is configured as an RBC/PLT detector for performing RBC measurement (measuring the number of red blood cells) and PLT measurement (measuring the number of platelets). The RBC/PLT detector D1 is capable of measuring RBC and PLT by a sheath flow-DC detection method.

The measuring section D2 is configured as an HGB detector for performing HGB measurement (measuring the amount of hemoglobin in the blood). The HGB detector is capable of measuring HGB by a SLS-hemoglobin method.

The measuring section D3 is configured as an optical detector for performing WBC measurement (measuring the number of white blood cells) and DIFF measurement (classifying white blood cells). The optical detector D3 is capable of performing the WBC measurement and the DIFF measurement by flow cytometry using a semiconductor laser. The structure of the third measuring section D3 is described in detail later. WBC measurement is a measurement for calculating the concentration of white blood cells in the sample, and the DIFF measurement is a measurement for classifying the white blood cells into lymphocytes, basophils, eosinophils, neutrophils, monocytes and the like, and calculating the concentration of each in the sample.

Figure 4:
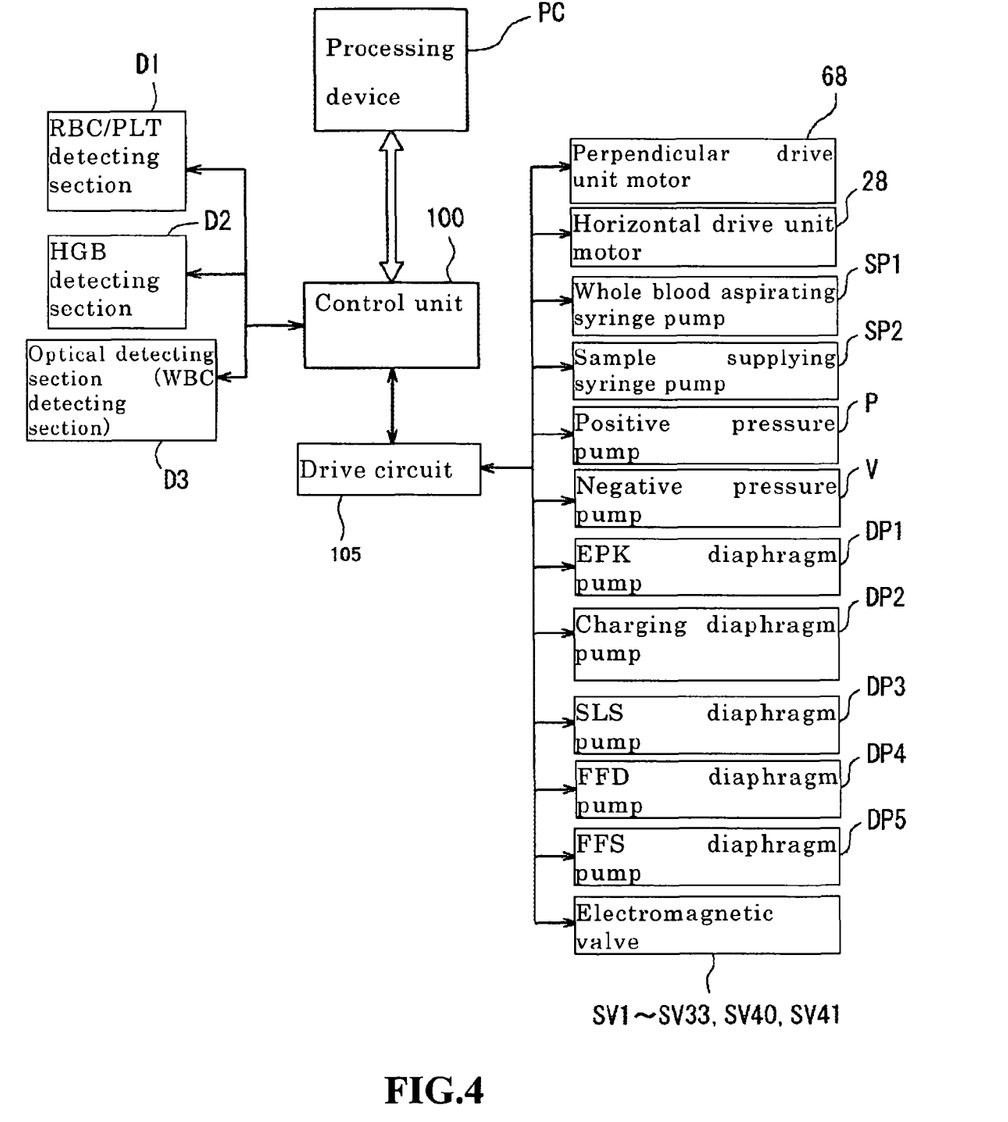
FIG. 4 is a control block diagram of the sample analyzer of FIG. 1.

As shown in FIG. 4, the sample analyzer S is further provided with a control unit 100 for controlling the measuring sections D1, D2, and D3. The sample analyzer S is also provided with a drive circuit 105, electromagnetic valves SV1 through SV33, SV40, and SV41 which are used when delivering sample and reagent, and various pumps and motors 28, 68, SP1, SP2, P, V, DP1, DP2, DP3, DP4, and DP5.

The control unit 100 controls the electromagnetic valves and various pumps and motors through the drive circuit 105. Furthermore, the control unit 100 is capable of communication with the processing device PC through a communication interface which is not shown in the drawing, and is capable of exchanging various types of signals and data with the processing device PC.

Figure 5:
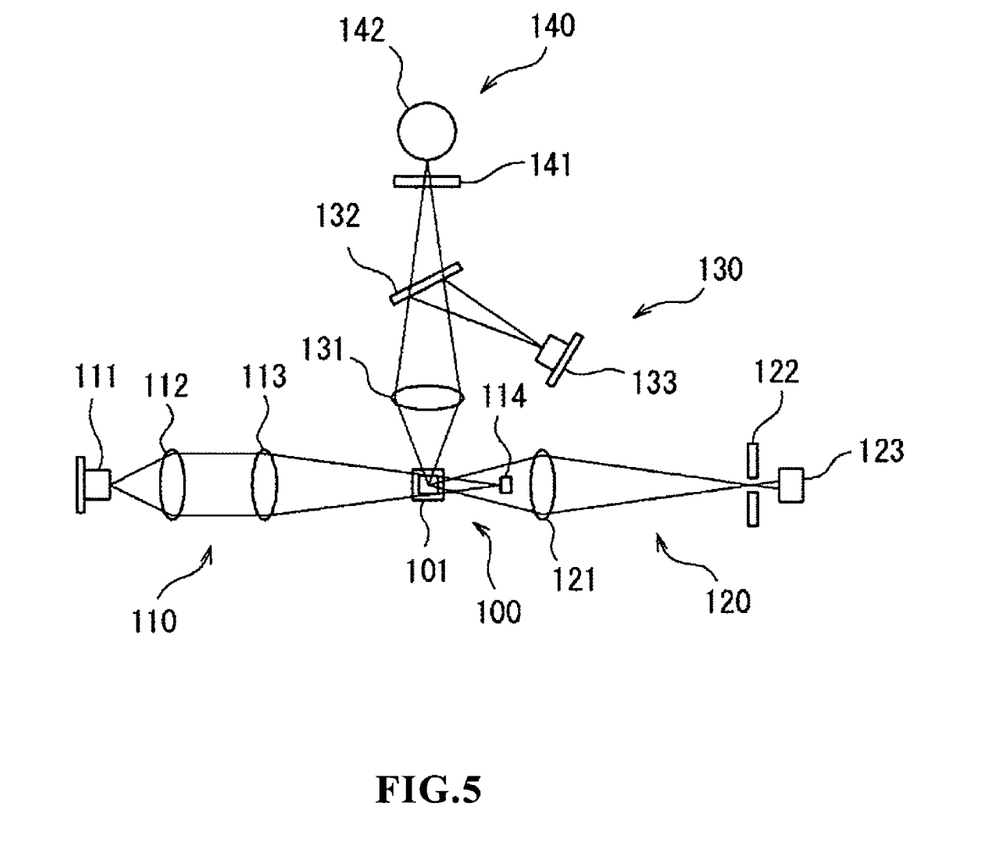
FIG. 5 is a brief structural view of the measuring section D3.

FIG. 5 briefly shows the structure of the measuring section D3. The measuring section D3 receives a measurement sample at a flow cell 101, generates a liquid flow in the flow cell 101, and irradiates and measures the cells contained in the liquid flow passing through the flow cell 101 by a beam emitted from the semiconductor laser; the measuring section D3 has a sheath flow system 90 beam spot forming system 110, forward scattered light receiving system 120, side scattered light receiving system 130, and side fluorescent light receiving system 140.

The sheath flow system 90 improves the accuracy, and reproducibility of cell counting by having a measurement sample flow within the flow cell 101 with the blood cells arrayed in a line and encapsulated by a sheath liquid. The beam spot system 110 is configured to irradiate the flow cell 101 with light emitted from a semiconductor laser 111 through a collimator lens 112 and a condenser lens 113. The beam spot system 110 is further provided with a beam stopper 114.

The forward scattered light receiving system 120 is configured to collect the light scattered in a forward direction using a forward collective lens 121, and receive the light which passes through a pinhole 122 by a photodiode (forward scattered light receiving unit) 123.

The side scattered light receiving system 130 is configured to collect the light scattered in a lateral direction using a side collective lens 131, reflect part of the light via a dichromatic mirror 132, and receive the light that passes through by a photodiode (side scattered light receiving unit) 133.

Light scattering is a phenomenon created by a change in the direction of travel of light due to the presence of particles such as blood cells which act as obstructions in the direction of travel of the light. Information related to the size and quality of a particle can be obtained by detecting the scattered light. In particular, information related to the size of a particle (blood cell) can be obtained from the forward scattered light. Moreover, information concerning the interior part of a particle can be obtained from the side scattered light. When a blood cell particle is irradiated by a laser beam, the intensity of the side scattered light is dependent on the complexity of the cell interior (shape of nucleus, size, density, and granularity). It is therefore possible to perform other measurements including the classification of white blood cells by using the characteristic of the intensity of the side scattered light.

The side fluorescent light receiving system 140 is configured to receive the light passing through the dichroic mirror 132 and subsequently passing through a spectral filter 141 using a photomultiplier (fluorescent light receiving unit) 142.

When light irradiates a fluorescing substance such as a stained blood cell, light is emitted which has a longer wavelength than the irradiating light. The intensity of the fluorescent light increases with the stain so that information relating to the degree of staining of the blood cell can be obtained by measuring the fluorescent light intensity. It is therefore possible to perform other measurements such as classification of white blood cells using the differences in (side) fluorescent light intensity.

Figure 6:
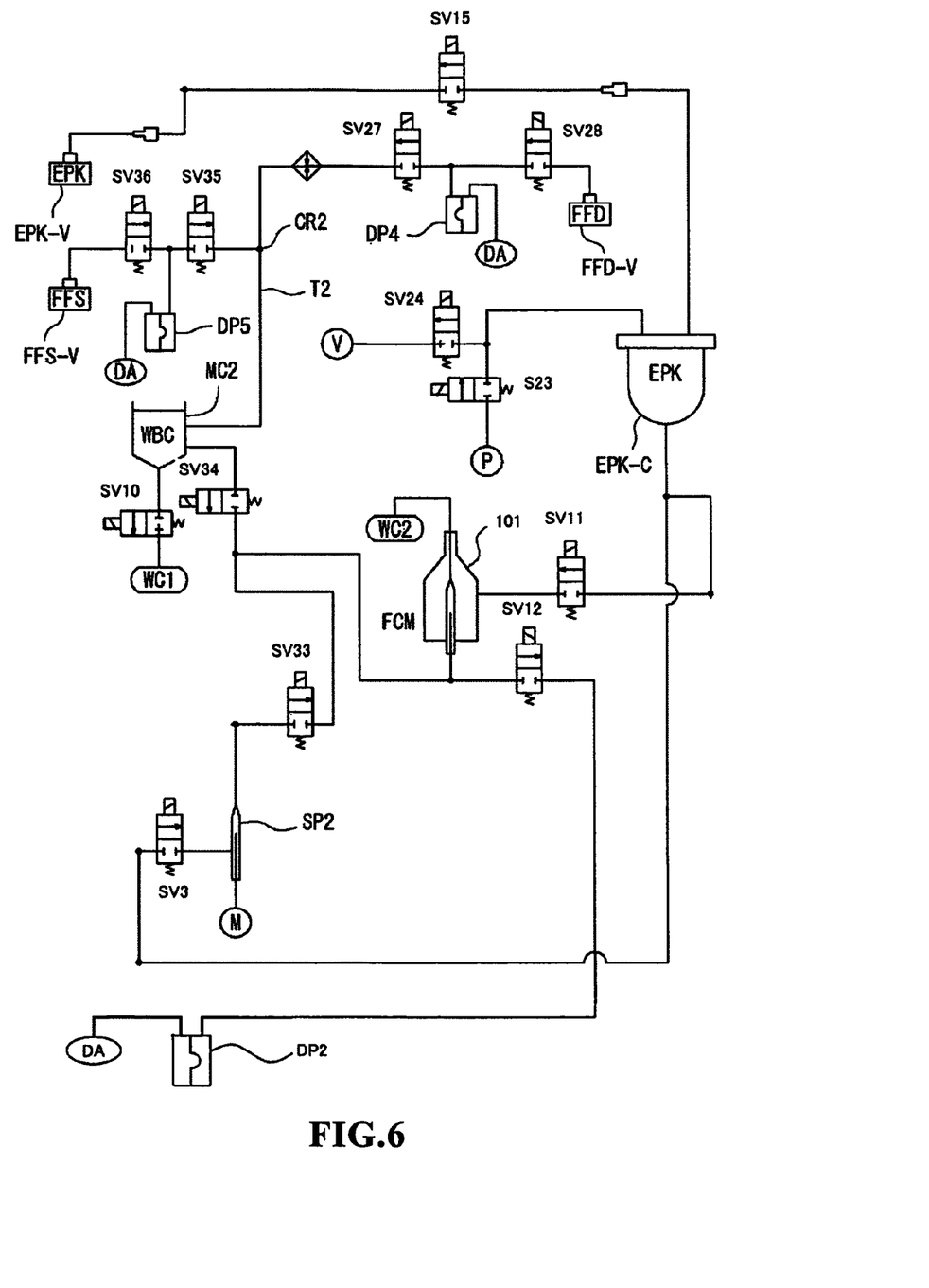
FIG. 6 is a fluid circuit diagram showing the fluid circuit of the WBC measuring system.

FIG. 6 is a flow circuit diagram showing the flow circuit of the WBC measuring system which is used for preparing the measurement samples in the second mixing chamber MC2, and WBC measurement (measuring the number of white blood cells) and DIFF measurement (classifying the white blood cells) performed by the measuring section D3.

As shown in the drawing, the flow circuit of the WBC measuring system includes the second mixing chamber MC2, flow cell 101 which is part of the measuring section D3, diaphragm pump DP4 for supplying hemolytic agent FFD to the second mixing chamber MC2, diaphragm pump DP5 for supplying staining solution FFS to the second mixing chamber MC2, and syringe pump SP2 for supplying a measurement sample to the flow cell 101.

Figure 7:
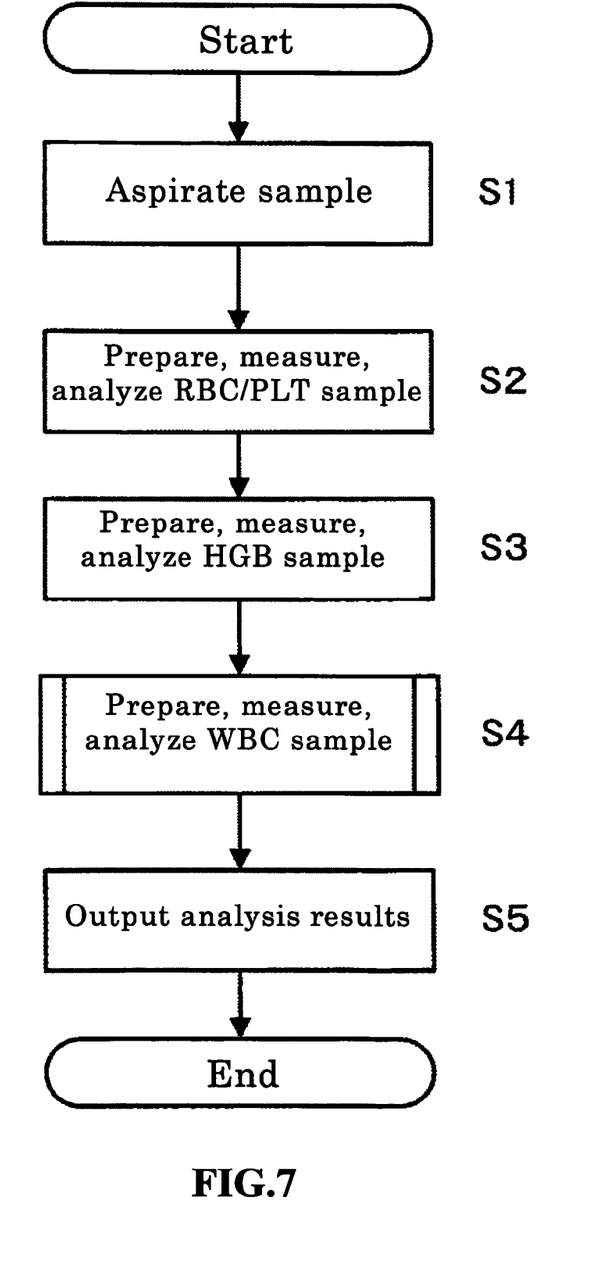
FIG. 7 is a flow chart showing the processing performed by the control unit 100 during sample analysis.

FIG. 7 is a flow chart showing the processing performed by the control unit 100 during sample analysis. When a user of the sample analyzer S inputs an instruction to start analysis, the control unit 100 executes a sample aspiration process in step S1. A predetermined amount of a sample is aspirated and retained in the aspirating tube 13 from a sample container 3 which has been placed in the sample receiving part 4. In the present embodiment, the amount of aspirated and retained sample in the aspirating tube 13 is 150 µl.

The control unit 100 then executes a process for the preparation, measurement, and analysis of RBC and PLT measurement samples in step S2. The amount of sample used for the RBC and PLT measurements is 4 µl. RBC and PLT measurement results are thus obtained. The amount of sample used for the RBC and PLT measurements is 4 µl.

The control unit 100 then executes a process for the preparation, measurement, and analysis of a Hgb measurement sample in step S3. In this process, the Hgb measurement sample is prepared, and Hgb is measured and analyzed by the measuring section D2. Hgb analysis results are thus obtained. The amount of sample used for the Hgb measurement is 2 µl.

The control unit 100 then executes a process for the preparation, measurement, and analysis of a WBC measurement sample in step S4. In this process, the WBC measurement sample is prepared in the second mixing chamber MC2, and WBC measurement and DIFF measurement are performed and the measurement results are analyzed by the measuring section D3. Analysis results relating to WBC are thus obtained. This process is described in detail later.

The processes of steps S2 to S4 are executed in parallel.

The control unit 100 then, in step S5, executes a process to output the analysis results obtained in steps S2 through S4 to the processing device PC, and the analysis of a single sample ends. The analysis results output to the processing device PC are displayed on the display of the processing device PC.

Figure 8:
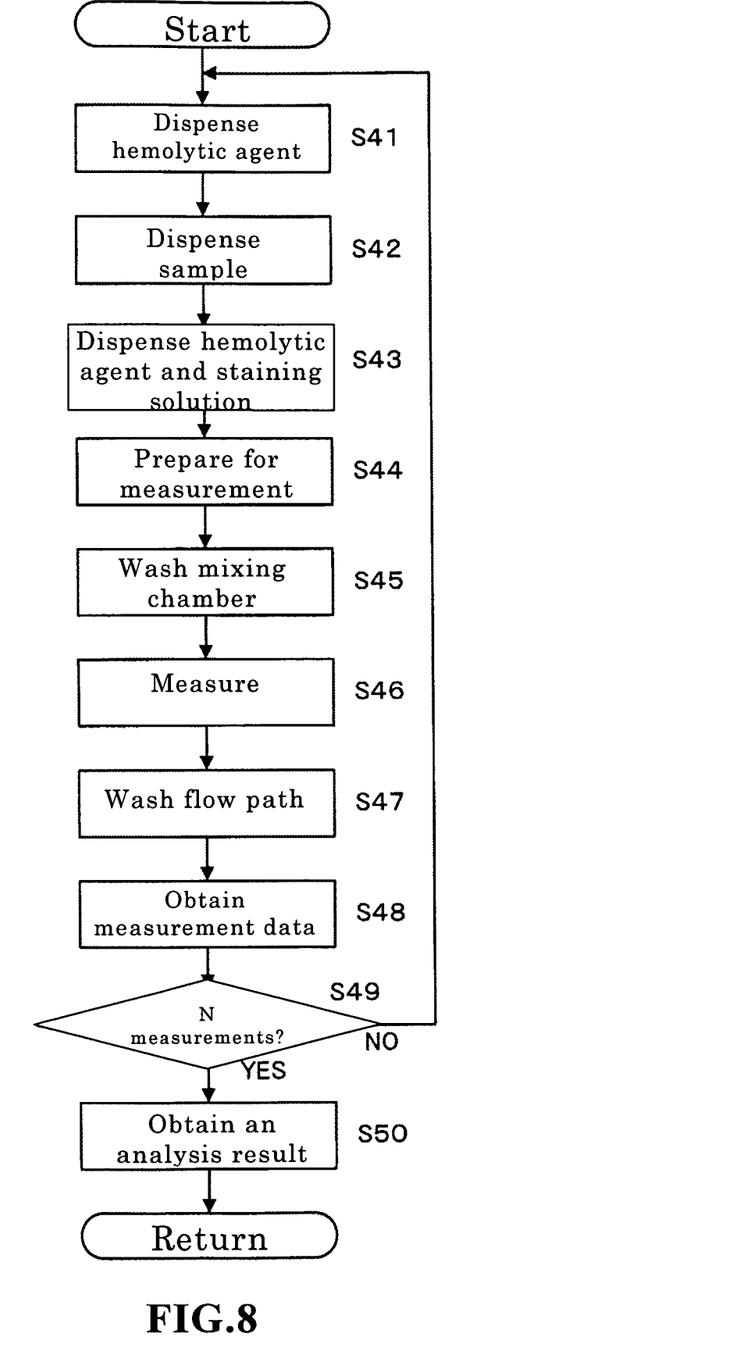
FIG. 8 is a flow chart showing details of the process of step S4 in the flow chart of FIG. 7.

The process of the WBC and DIFF measurement sample preparation, measurement and analyses in step S5 is described in detail below using the flow circuit diagram of FIG. 6 and the flow chart of FIG. 8.

In the process of the preparation, measurement, and analysis of the WBC and DIFF samples, the control unit 100 first executes a process to dispense hemolytic agent FFD to the second mixing chamber MC2 in step S41. In the process of step S41, the electromagnetic valves SV27 and SV28 are opened, and the diaphragm pump DP4 delivers 500 µl of hemolytic agent FFD to the second mixing chamber MC2.

In step S42, the control unit 100 then executes a process to dispense 20 µl of the sample within the aspirating tube 13 to the second mixing chamber MC2. In the process of step S42, the aspirating tube 13 moves above the second mixing chamber MC2 and discharged 20 µl of the sample in the aspirating tube 13 into the second mixing chamber MC2. The amount of sample remaining in the aspirating tube 13 at this time is 124 µl since 4 µl has been used for the RBC and PLT measurements, and 2 µl has also been used for the Hgb measurement among the 150 µl of sample retained in the aspirating tube 13 (124 µl=150 µl−4 µl−2 µl−20 µl).

The control unit 100 then executes a process to dispense hemolytic agent FFD and staining solution FFS to the second mixing chamber MC2 in step S43. In the process of step S43, the electromagnetic valves SV27 and SV28 are opened, and the diaphragm pump DP4 delivers 500 µl of hemolytic agent FFD to the second mixing chamber MC2. Then the electromagnetic valves SV35 and SV36 are opened, and the diaphragm pump DP5 delivers 20 µl of staining solution FFS to the second mixing chamber MC2. Thus, a measurement sample is prepared in the second mixing chamber MC2.

The control unit 100 then executes a measurement preparation process in step S44. In the process of step S44, the electromagnetic values SV12 and SV13 are opened, and the diaphragm pump DP2 performed an aspirating operation to fill the flow path with measurement sample from the second mixing chamber MC2 to the diaphragm pump DP2.

The control unit 100 then executes a process to wash the second mixing chamber MC2 in step S45. In the process of step S45, the electromagnetic valves SV10, SV27, and SV28 are opened, the hemolytic agent FFD in the second mixing chamber MC2 is flows to a waste chamber WC1 via the negative pressure therein so as to be discharged into the waste chamber WC1. The second mixing chamber is thus washed. Adverse effects on a subsequent measurement caused by residual washing fluid in the second mixing chamber MC2 can thus be reduced by washing the second mixing chamber MC2 using hemolytic agent FFD, which is a reagent that will be used in the preparation of the next measurement sample, as a washing solution.

The control unit 100 then executes a process to measure the measurement sample in step S46. In the process of step S46, the electromagnetic valve SV33 is opened, and the measurement sample filling the flow path in step S44 caused to flow through the flow cell 101 via a discharge operation performed by the syringe pump SP2. Furthermore, a positive pressure pump P is actuated by opening the electromagnetic valves SV11 and SV23, which causes a dilution fluid EPK to flow through the flow cell 101 to form a flow cell. The photomultiplier 142 receives the fluorescent light of the forward scattered light and side scattered light at this time, and the photodiodes 132 and 133 (refer to FIG. 5)transmit signals representing the amounts of light to the control unit 100.

The control unit 100 then executes a process to wash the flow path from the second mixing chamber MC2 to the diaphragm pump DP2 in step S47. In the process of step S47, the electromagnetic valves SV3, SV12, and SV33 are opened, and dilution solution EPK passes through the electromagnetic valve SV3, syringe pump SP2, and electromagnetic valves SV33 and SV12 when the diaphragm pump SP2 performs an aspirating operation. The flow path is thus washed. Moreover, the flow cell 101 may also be washed in the process of step S47 by opening the electromagnetic valve SV11.

Figure 9:
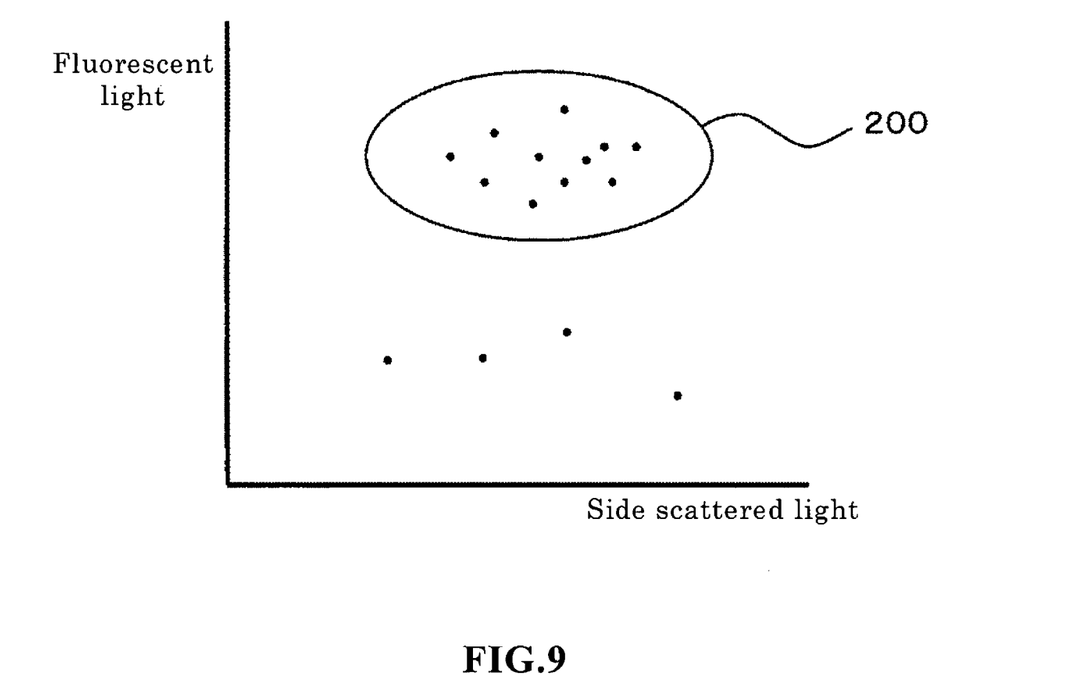
FIG. 9 shows a scattergram created in step S48 in the flow chart of FIG. 8.

Then in step S48, the control unit 100 executes a process to obtain the measurement data of the measurement sample which was measured in step S46. In the process of step S48, a scattergram is created as measurement data using the signals transmitted to the control unit 100 from the photodiodes 123 and 133, and the photomultiplier 142 in step S46. FIG. 9 shows an example of a scattergram prepared at this time. The control unit 100 determines that the blood cells contained in screen region 2000 are WBC, and obtains the number (that is, the concentration) of WBC contained in a predetermined amount of sample) as measurement data by counting these blood cells. The control unit 100 similarly obtains measurement data for other items. The control unit 100 also classifies WBC into lymphocyte, basophil, eosinophil, neutrophil, and monocyte categories, and calculates the respective concentrations. The number of WBC in spinal fluid, the number of blast cells in peripheral blood, and the number of WBC in platelet products are given as examples of the measurement data obtained in step S48.

In step S49, the control unit 100 then determines whether or not the number of executions (that is the number of measurements of measurement sample) of the processes from step S41 through S48 has reached a predetermined number (for example, 7). In FIG. 8, "N" is not specifically limited insofar as "N" is an integer of 2 or greater. Furthermore, this "N" may also be the "N" of a setting unit provided in the processing device PC or the sample analyzer so as to be modifiable by the users of the sample analyzer S.

When it is determined that the number of measurements of the measurement sample has not attained a predetermined number, the control unit 100 again executes the processes from step S41 through step S48. In this case, 20 µl of the remaining 124 µl of sample remaining in the aspirating tube 13 is discharged into the second mixing chamber MC2 in step S42. The amount of sample remaining in the aspirating tube 13 is therefore 104 µl (=124 µl−20 µl).

The processes from step S41 through S48 are performed until the number of measurements of the measurement sample attains a predetermined number. When the number of measurements of the measurement sample reaches the predetermined number (that is, when the determination is YES in step S49), the control unit 100 executes a process to obtain an analysis result in step S50. In the process of step S50, a process is executed to average a plurality of measurement data obtained for predetermined items in step S48. For example, when "N" is 7, a process is executed to average seven WBC counts since the number of WBC has been obtained seven times (that is, the process of step S48 has been executed seven times). This averaging process need not use all seven obtained WBC counts and may, for example, average five measurement data by excluding the maximum measurement data and the minimum measurement data. Moreover, rather than averaging, the measurement data positioned most intermediately among the seven measurement data (for example, the median value) may be used as the analysis result.

The amount of sample can be increased to obtain analysis result for a predetermined item of a single sample by performing the previously mentioned WBC and DIFF sample preparation measurement, and analysis process. High precision analysis is therefore possible even when there is a low concentration of the substance being measured in the sample. The amount of reagent used for one sample preparation is not increased compared to conventional apparatuses since a sample aspirated from a sample container 3 is divided and used in the process of WBC and DIFF sample preparation, measurement and analysis. Therefore, increasing the size of the apparatus can be avoided.

In the present embodiment, the second mixing chamber MC2 is washed in step S45, and the flow path is washed in step S47, however, these washings may also be omitted. 1 In the analysis of a single sample there is minimal affect on the measurement of a subsequent measurement sample even when washing is omitted in the chamber and flow path because the measurement sample retained in the chamber and the flow path has been prepared from the same sample.

In the present embodiment, analysis results are obtained by obtaining the WBC counts obtained based on scattergrams in step S48, and in step S50 averaging the number of a plurality of WBC counts obtained in a plurality of executions in step S48. The present invention is not limited to this arrangement inasmuch as, in step S50, a single scattergram may be prepared to obtain a WBC count as an analysis result based on this scattergram by overlaying a plurality of scattergrams obtained by a plurality of executions of step S48.

The processes of steps S41 through S48 are executed in parallel. That is, the process of a subsequent step is started before the process of the previous step has ended. This parallel processing is described using FIG. 10. Each row of FIG. 10 respectively represents a process among the processes of steps S41 through S48, and the horizontal axis represents the passage of time. The horizontal line indicated in each row represents the period during which the process is being executed. In the drawing, "N" is 4 in order to simplify the description.

Figure 10:
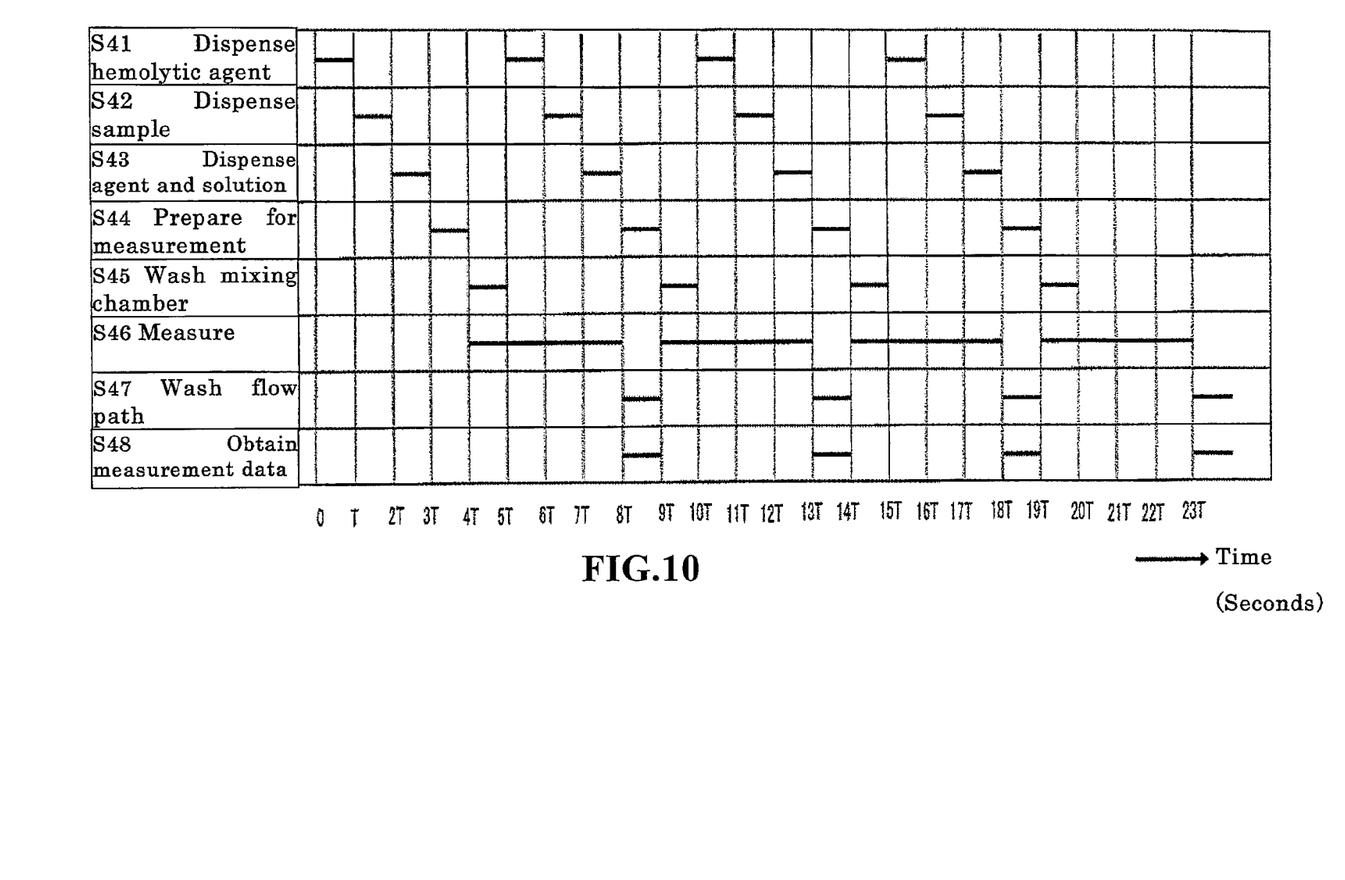
FIG. 10 is a timing chart showing the timing of the processing from step S41 to step S48 in the flow chart of FIG. 8.

As shown in the drawing, the hemolytic agent dispensing process of step S41 is executed for T seconds from 0 seconds to T seconds. The sample dispensing process of step S42 is executed for T seconds from T seconds to 2T seconds. The hemolytic agent and staining solution dispensing process of step S43 is executed for T seconds from 2T seconds to 3T seconds. The measurement preparation process of step S44 is executed for T seconds from 3T seconds to 4T seconds. The mixing chamber washing process of step S45 is executed for T seconds from 4T seconds to 5T seconds. The measurement process of step S46 is executed for 4T seconds from 4T seconds to 8T seconds and is executed in parallel with the mixing chamber washing process of step S45. The hemolytic agent dispensing process of the second step S41 is executed for T seconds from 5T seconds to 6T seconds, and is executed in parallel with the measurement process of step S46. The sample dispensing process of the second step S42 is executed for T seconds from 6T seconds to 7T seconds, and is executed in parallel with the measurement process of step S46. The hemolytic agent and staining solution dispensing process of the second step S43 is executed for T seconds from 7T seconds to 8T seconds, and is executed in parallel with the measurement process of step S46. The measurement preparation process of the second step S44 is executed for T seconds from 8T seconds to 9T seconds. The flow path washing process of step S47 and the measurement data obtaining process of step S48 are executed for T seconds from 8T seconds to 9T seconds in parallel with the measurement preparation process of step S44. The first measurement data are obtained at time 9T seconds. The mixing chamber washing process of the second step S45 is executed for T seconds from 9T seconds to 10T seconds. The measurement process of the second step S46 is executed for 4T seconds from 9T seconds to 13T seconds in parallel with the mixing chamber washing process of the second step S45. Subsequently, the processes of steps S41 through S48 are similarly executed for the third and fourth measurements.

The time until analysis results are obtained can be reduced by executing the various processes in parallel. Sample processing performance can be therefore improved.

In the present embodiment, the end of the hemolytic agent and staining solution dispensing process of step S43, that is the time from the end of measurement sample preparation to the start of the measuring process of step S46, is completely identical (T seconds) in first through fourth measurements. That is, the time from the addition of reagent to the sample until the measurement sample is measured is identical in the first through fourth measurements according to the configuration of the sample analyzer. The reaction time of the sample and reagents is therefore identical in the first through fourth measurements, and measurement error caused by differences in reaction time can be avoided. High-precision analysis is therefore possible.

Furthermore, although the processing periods of steps S41 through S45, S47, and S48 are all an identical T seconds in the drawing, these processing periods are used to simplify the description, it is unnecessary to have these processing periods invariably identical.

Although the measurement sample is sequentially prepared within the first mixing chamber in the above embodiment, the present invention is not limited to this arrangement inasmuch as the sample analyzer may also be provided with a plurality of mixing chambers so that a measurement sample may also be prepared within the respective mixing chambers.

Although the sample aspirated from a sample container is retained in the aspirating tube in the above embodiment, the present invention is not limited to this arrangement inasmuch as the sample analyzer may be provided with a sample retention vessel to retain the sample so that a sample aspirated from a sample container may also be retained in the sample retention vessel. In this case, sample is distributed from the sample retention vessel to the mixing chamber. The sample retention vessel may also be washed and reused, or the vessel may be disposable.

Although the mixing ratios of the sample, hemolytic agent, and staining solution are identical for a plurality of reagents used for measurement in the present embodiment, the present invention is not limited to this arrangement inasmuch as the mixing ratio may also be changed for each reagent used for measurement.

Although an apparatus for analyzing blood components in a sample has been described in the above embodiment, the present invention is not limited to this arrangement inasmuch as the present invention may be applied to apparatuses for analyzing other components contained within a body, and the present invention may also be applied to industrial analyzers for analyzing components and the like of toner and cosmetics.

The invention claimed is:

1. A sample analyzer comprising:
a retaining section for retaining a sample aspirated from a sample container;
a sample preparing section that includes a mixing chamber to prepare a measurement sample by using a part of the sample retained in the retaining section and a reagent for measuring a predetermined item;
a measuring section that includes a measurement device that measures the measurement sample prepared by the sample preparing section, and obtains measurement data; and
a control unit configured to:
control the sample preparing section to sequentially prepare a plurality of measurement samples from the retained sample, wherein a mixing ratio of the part of the sample and the reagent is substantially identical for each of the plurality of measurement samples; and
control the measuring section to sequentially measure the plurality of measurement samples, and to obtain a plurality of measurement data; and
obtain a statistical analysis result of the predetermined item of the sample based on the plurality of measurement data obtained by the measuring section.

2. The sample analyzer of claim 1, wherein the retaining section comprises a pipette for aspirating the sample from the sample container.

3. The sample analyzer of claim 1, wherein the mixing chamber is connected to the measurement device such that the control unit controls the sample preparing section and the measuring section so that a processing time from an end of the measurement sample preparation until a start of a measurement of a measurement sample is substantially identical for each of the plurality of measurement samples.

4. The sample analyzer of claim 1, wherein the control unit creates a scattergram based on the plurality of measurement data.

5. The sample analyzer of claim 1, wherein the mixing chamber is arranged with the measurement device such that the control unit controls the sample preparing section and the measuring section so that while the measuring section is measuring a certain measurement sample prepared by using a part of the sample, the sample preparing section starts preparing a next measurement sample by using another part of the sample, the next measurement sample being measured by the measuring section after the certain measurement sample.

6. The sample analyzer of claim 1, wherein the statistical analysis result comprises any one of an average value of the plurality of measurement data, an average of some of the plurality of measurement data, and a measurement data positioned most intermediately among the plurality of measurement data.

7. The sample analyzer of claim 1, wherein the measurement device includes a blood cell counter and the statistical analysis result of the predetermined item comprises an analysis result relating to a number of blood cells.

8. The sample analyzer of claim 7, wherein the measurement device includes a blood cell counter and the sample comprises a body fluid, and wherein the predetermined item comprises a number of white blood cells.

9. The sample analyzer of claim 1, wherein the measurement device includes a blood cell counter and the sample comprises a blood sample, and wherein the predetermined item comprises a number of blast cells or a number of megakaryocytes.

10. The sample analyzer of claim 1, wherein:
the mixing chamber is a mixing chamber for white blood cell measurement configured to prepare a measurement sample for white blood cell measurement;
the sample preparing section further comprises a mixing chamber for red blood cell measurement configured to prepare a measurement sample for red blood cell measurement;
the measurement device comprises a white blood cell detector connected to the mixing chamber for white blood cell measurement, and a red blood cell detector connected to the mixing chamber for red blood cell measurement.

* * * * *